United States Patent
Protzmann et al.

(10) Patent No.: US 8,049,030 B2
(45) Date of Patent: Nov. 1, 2011

(54) METHOD FOR PRODUCING (METH)ACRYLATES

(75) Inventors: Guido Protzmann, Bensheim (DE); Harald Trauthwein, Buerstadt (DE); Joachim Knebel, Alsbach-Haehnlein (DE); Thorben Schuetz, Seeheim-Jugenheim (DE); Gerhard Koelbl, Gernsheim (DE); Thomas Kehr, Muehltal (DE); Guenther Lauster, Worms (DE)

(73) Assignee: Evonik Röhm GmbH, Darmstadt (DE)

( * ) Notice: Subject to any disclaimer, the term of this patent is extended or adjusted under 35 U.S.C. 154(b) by 0 days.

(21) Appl. No.: 12/667,599

(22) PCT Filed: May 8, 2008

(86) PCT No.: PCT/EP2008/055667
§ 371 (c)(1),
(2), (4) Date: Apr. 9, 2010

(87) PCT Pub. No.: WO2009/003744
PCT Pub. Date: Jan. 8, 2009

(65) Prior Publication Data
US 2010/0204509 A1    Aug. 12, 2010

(30) Foreign Application Priority Data
Jul. 5, 2007  (DE) .......................... 10 2007 031 470

(51) Int. Cl.
*C07C 67/02*    (2006.01)
(52) U.S. Cl. ....................................... 560/217; 570/217
(58) Field of Classification Search ................... 560/217
See application file for complete search history.

(56) References Cited

U.S. PATENT DOCUMENTS 4,745,213 A * 5/1988 Schlosser et al. ............. 560/217
6,008,371 A   12/1999 Knebel et al.

FOREIGN PATENT DOCUMENTS

CN   1747924 A    3/2006
GB   1 094 998    12/1967

OTHER PUBLICATIONS

U.S. Appl. No. 12/667,604, filed Jan. 4, 2010, Schmitt, et al.
U.S. Appl. No. 12/667,822, filed Jan. 5, 2010, Knebel, et al.
U.S. Appl. No. 12/667,538, filed Jan. 4, 2010, Knebel, et al.
U.S. Appl. No. 08/373,422, filed Jan. 17, 1995, Knebel, et al.
U.S. Appl. No. 12/990,095, filed Oct. 28, 2010, Knebel.
Chinese Office Action mailed Feb. 14, 2011w/English translation.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The present invention relates to a process for preparing (meth)acrylates, which comprises the transesterification of an alcohol with a low-boiling ester of (meth)acrylic acid in the presence of catalysts, with the alcohol liberated from the low-boiling ester of (meth)acrylic acid being separated off by distillation, characterized in that the molar ratio of low-boiling ester of (meth)acrylic acid to starting alcohol present in the reaction mixture is increased during the reaction by addition of low-boiling ester of (meth)acrylic acid. The process of the invention makes a particularly inexpensive preparation of (meth)acrylates having a very high purity possible.

31 Claims, No Drawings

METHOD FOR PRODUCING (METH)ACRYLATES

The present invention relates to a process for preparing (meth)acrylates.

(Meth)acrylates are widely known and frequently used monomers. Accordingly, a variety of methods of obtaining these compounds are known. To prepare specialty (meth) acrylates, transesterification reactions in which methyl methacrylate is reacted with an appropriate alcohol are frequently carried out. Various catalysts have hitherto been used to improve the yield and the selectivity of the reaction.

For example, the publication DE 28 05 702 describes the preparation of esters of unsaturated carboxylic acids. To catalyse the reactions described, it is possible to use, in particular, compounds which contain zirconium and/or calcium. Particularly suitable catalysts include, in particular, zirconium acetylacetonate. The reactions lead to high yields of about 97%, based on the alcohol used.

Furthermore, acids or bases can be used for catalysing the transesterification. Such reactions are disclosed, for example, in CN 1355161, DE 34 23 443 or EP-A-0 534 666. Basic catalysts include, in particular, lithium amide, as is disclosed, for example, in the publications DE 34 23 443, CA 795814 and U.S. Pat. No. 6,194,530.

Furthermore, addition of the starting compounds during the course of the reaction has been proposed in order to improve the economics of the preparation. Thus, for example, the publication U.S. Pat. No. 5,072,027 describes addition of alcohol and methyl methacrylate after a high conversion of the starting compounds used at the beginning of the reaction. An increase in the molar ratio during the reaction is not described in this publication.

The abovementioned reactions lead to a high yield and to pure products. However, owing to the high economic importance of specialty (meth)acrylates, efforts are continually being made to improve the preparation of these compounds further.

OBJECT

In view of the prior art, it was an object of the present invention to provide a process for preparing (meth)acrylates, in which the product can be obtained very economically. In addition, the (meth)acrylate obtained should contain only very small amounts of by-products and catalyst residues.

A further object of the invention was to invent a process in which (meth)acrylates can be obtained very selectively.

In addition, it was an object of the present invention to provide a process for preparing (meth)acrylates which can be carried out simply and inexpensively. The product should here be obtained in high yields and, viewed overall, with a low energy consumption.

SOLUTION

These objects and further objects which are not explicitly mentioned but can readily be derived or deduced from the relationships discussed here are achieved by a process having all features of Claim 1. Advantageous modifications of the process of the invention are protected in the dependent claims which refer back to Claim 1.

The present invention accordingly provides a process for preparing (meth)acrylates, which comprises the transesterification of an alcohol with a low-boiling ester of (meth) acrylic acid in the presence of catalysts, with the alcohol liberated from the low-boiling ester of (meth)acrylic acid being separated off by distillation, which is characterized in that the molar ratio of low-boiling ester of (meth)acrylic acid to starting alcohol present in the reaction mixture is increased during the reaction by addition of low-boiling ester of (meth) acrylic acid.

This makes it possible, in an unforeseeable way, to provide a process for preparing (meth)acrylates, in which the product is obtained very economically. The product obtained surprisingly contains only very small amounts of by-products and catalyst residues.

Furthermore, the process of the invention makes a particularly selective preparation of (meth)acrylates possible.

In addition, the process of the invention can be carried out simply and inexpensively and the product can be obtained in high yields and, viewed overall, with a low energy consumption.

In addition, a particularly high utilization of the volume of the reactor can be achieved by means of the process of the invention, so that large amounts of specialty (meth)acrylates can be produced even in relatively small plants. Furthermore, the amount of specialty (meth)acrylate produced per batch can be increased, so that it is possible to achieve further advantages since the costs for carrying out the reaction, based on the amount of product obtained, decrease.

According to the invention, (meth)acrylates are prepared, with the expression (meth)acrylate referring to methacrylate, acrylate and mixtures of methacrylates and acrylates. (Meth) acrylates are well known per se. These compounds include, inter alia, (meth)acrylates derived from saturated alcohols, e.g. hexyl (meth)acrylate, 2-ethylhexyl (meth)acrylate, heptyl (meth)acrylate, 2-(tert-butylamino)ethyl (meth)acrylate, octyl (meth)acrylate, 3-isopropylheptyl (meth)acrylate, nonyl (meth)acrylate, decyl (meth)acrylate, undecyl (meth) acrylate, 5-methylundecyl (meth)acrylate, dodecyl (meth) acrylate, 2-methyldodecyl (meth)acrylate, tridecyl (meth) acrylate, 5-methyltridecyl (meth)acrylate, tetradecyl (meth) acrylate, pentadecyl (meth)acrylate, hexadecyl (meth) acrylate, 2-methylhexadecyl (meth)acrylate, heptadecyl (meth)acrylate, 5-isopropylheptadecyl (meth)acrylate, 4-tert-butyloctadecyl (meth)acrylate, 5-ethyloctadecyl (meth)acrylate, 3-isopropyloctadecyl (meth)acrylate, octadecyl (meth)acrylate, nonadecyl (meth)acrylate, eicosyl (meth) acrylate, cetyleicosyl (meth)acrylate, stearyleicosyl (meth) acrylate, docosyl (meth)acrylate and/or eicosyltetratriacontyl (meth)acrylate;

(meth)acrylates derived from unsaturated alcohols, e.g. 2-propynyl (meth)acrylate, allyl (meth)acrylate, vinyl (meth) acrylate, oleyl (meth)acrylate; cycloalkyl (meth)acrylates, e.g. cyclopentyl (meth)acrylate, 3-vinylcyclohexyl (meth) acrylate, cyclohexyl (meth)acrylate, bornyl (meth)acrylate; (meth)acrylates having two or more (meth)acryl groups, glycol di(meth)acrylates, e.g. ethylene glycol di(meth)acrylate, diethylene glycol di(meth)acrylate, triethylene glycol di(meth)acrylate, tetraethylene and polyethylene glycol di(meth)acrylate, 1,3-butanediol (meth)acrylate, 1,4-butanediol (meth)acrylate, 1,6-hexanediol di(meth)acrylate, glycerol di(meth)acrylate and dimethacrylates of ethoxylated bisphenol A; (meth)acrylates having three or more double bonds, e.g. glycerol tri(meth)acrylate, trimethylolpropane tri (meth)acrylate, pentaerythritol tetra(meth)acrylate and dipentaerythritol penta(meth)acrylate.

Particularly suitable (meth)acrylates include, in particular, ethylene glycol dimethacrylate (1,2-ethanediyl di-2-methylpropenoate; CAS number 97-90-5), 1,3-butanediol dimethacrylate (CAS number 1189-08-8), 1,4-butanediol dimethacrylate (CAS number 2082-81-7) and/or trimethylolpropane trimethacrylate.

The (meth)acrylates are, according to the invention, prepared using an alcohol which will hereinafter also be referred to as starting alcohol. The type of alcohol is determined by the intended target compound. Accordingly, it is possible to use, in particular, alcohols having 5 or more carbon atoms, unsaturated alcohols and/or polyhydric alcohols. Preferred alcohols having 5 or more carbon atoms include, for example, pentanol, hexanol, 2-ethylhexanol, heptanol, 2-tert-butylheptanol, octanol, 3-isopropylheptanol, nonanol, decanol, undecanol, 5-methylundecanol, dodecanol, 2-methyldodecanol, tridecanol, 5-methyltridecanol, tetradecanol, pentadecanol, hexadecanol, 2-methylhexadecanol, heptadecanol, 5-isopropyl-heptadecanol, 4-tert-butyloctadecanol, 5-ethyloctadecanol, 3-isopropylocta-decanol, octadecanol, nonadecanol, eicosanol, cetyleicosanol, stearyleicosanol, docosanol and/or eicosyltetratriacontanol. Preferred unsaturated alcohols include, in particular, 2-propyn-1-ol, allyl alcohol and vinyl alcohol and/or oleyl alcohol.

Particular preference is given to using polyhydric alcohols. Polyhydric alcohols are organic compounds having two, three, four or more hydroxy groups. These compounds include, in particular, ethylene glycol, trimethylolpropane, 1,2-propanediol, 1,3-propanediol, 1,3-butanediol, 1,4-butanediol, 1,6-hexanediol, pentaerythritol, polyethylene glycol, in particular polyethylene glycol 400, and/or glycerol, with trimethylolpropane being particularly preferred. The compounds are frequently commercially available, for example from BASF AG or Celanese AG.

According to the present invention, an alcohol is reacted with a low-boiling ester of (meth)acrylic acid. The term "low-boiling ester" means that the ester used as starting compound has a lower boiling point than the ester obtained by means of the transesterification. At a pressure of 10 mbar, the difference between the boiling points is preferably at least 2° C., particularly preferably at least 10° C. and very particularly preferably at least 20° C. Particularly suitable (meth)acrylates are formed by, in particular, alcohols having from 1 to 4 carbon atoms. These include, in particular, methanol, ethanol, n-propanol, isopropanol, n-butanol and tert-butanol. Particular preference is given to using, in particular, ethyl (meth)acrylate or methyl (meth)acrylate, with methyl methacrylate being very particularly preferred.

The weight ratio of starting alcohol to the low-boiling ester of methacrylic acid is preferably in the range from 1:2 to 1:20, particularly preferably from 1:5 to 1:15 and very particularly preferably in the range from 1:6 to 1:10.

The transesterification according to the invention preferably takes place in the presence of catalysts. The catalysts which can be used for this purpose are well known per se and are described comprehensively in the abovementioned prior art. They include, in particular, compounds of zirconium such as zirconium acetylacetonate. The CAS number of zirconium acetylacetonate is 17501-44-9. The preparation of zirconium acetylacetonate from acetylacetone (pentane-2,4-dione) and zirconium compounds is described, for example, in Houben-Weyl, Methoden der organischen Chemie, 4th Edition, Vol. VI/2, 1963, pages 53-55 and 58 to 61, and in A. E. Martell, M. Calvin, "Die Chemie der Metallchelatverbindungen" (1958). From 0.2 to 5 mmol, particularly preferably from 0.5 to 2 mmol, of zirconium acetylacetonate per mole of alcohol to be transesterified can advantageously be used. The catalyst can also be prepared in situ, with the starting materials being able to be added to the reaction mixture either before or during the transesterification.

It can be particularly advantageous to use, in particular, catalysts comprising lithium compounds and/or calcium compounds, with at least one of the compounds of lithium and/or of calcium being an oxide, a hydroxide, an alkoxide having from 1 to 4 carbon atoms or a carboxylate having from 1 to 4 carbon atoms. The catalyst preferably comprises at least one lithium compound selected from the group consisting of lithium chloride (LiCl), lithium amide ($LiNH_2$), lithium oxide ($Li_2O$), lithium hydroxide (LiOH), lithium alkoxide having from 1 to 4 carbon atoms, e.g. lithium methoxide ($Li(CH_3O)$), lithium ethoxide ($Li(CH_3CH_2O)$), and/or lithium carboxylate having from 1 to 4 carbon atoms, for example lithium acetate, and at least one calcium compound selected from the group consisting of calcium oxide (CaO), calcium hydroxide ($Ca(OH)_2$), calcium alkoxide having from 1 to 4 carbon atoms, e.g. calcium methoxide ($Ca(CH_3O)_2$), calcium ethoxide ($Ca(CH_3CH_2O)_2$), and/or calcium carboxylate having from 1 to 4 carbon atoms, for example calcium acetate.

The compounds of lithium and/or of calcium can preferably be basic in nature, i.e. dissolution in water results in an increase in the pH.

The catalyst can advantageously contain, for example, lithium hydroxide (LiOH), lithium oxide ($Li_2O$), lithium methoxide ($Li(CH_3O)$), and/or lithium ethoxide ($Li(CH_3CH_2O)$) as lithium compound.

Further catalysts of particular interest are catalysts which comprise calcium oxide (CaO), calcium hydroxide ($Ca(OH)_2$), calcium methoxide ($Ca(CH_3O)_2$) and/or calcium ethoxide ($Ca(CH_3CH_2O)_2$) as calcium compound.

Preference is given to using a mixture comprising lithium hydroxide and calcium oxide or lithium hydroxide and calcium hydroxide as catalyst. These mixtures are particularly advantageous for the transesterification of butanediols.

In a further embodiment, a mixture comprising lithium amide ($LiNH_2$) and lithium chloride (LiCl) can be used as catalyst. This mixture is useful, for example, for preparing ethylene glycol dimethacrylate.

Furthermore, combinations comprising lithium chloride (LiCl) and calcium oxide (CaO) are particularly advantageous catalysts. These catalysts can be used, in particular, for preparing trimethylolpropane trimethacrylate.

The amount of catalyst used can be within a wide range. However, processes in which the proportion of catalyst, based on the weight of the alcohol used, is in the range from 0.05 to 8% by weight, preferably in the range from 0.01 to 5% by weight and particularly preferably in the range from 0.1 to 1% by weight, are of particular interest.

The total amount of catalyst used can be added to the reaction mixture at the beginning of the reaction. In a particularly advantageous modification, part of the catalyst, for example part of the lithium amide, can be added to the reaction mixture during the course of the reaction. Preference is given to adding further catalyst to the reaction mixture after a conversion in the range from 20 to 80%, particularly preferably in the range from 30% to 60%, based on the weight of the alcohol used.

The reaction can be carried out under superatmospheric or subatmospheric pressure. In a particularly advantageous modification of the present invention, the transesterification can be carried out at a pressure in the range from 200 to 2000 mbar, particularly preferably in the range from 500 to 1300 mbar.

The reaction temperature can, especially as a function of the pressure, likewise be within a wide range. In a preferred embodiment of the present invention, the reaction is preferably carried out at a temperature in the range from 60° C. to 150° C., particularly preferably in the range from 70° C. to 140° C. and very particularly preferably from 90 to 130° C.

Particular advantages can surprisingly be achieved if the temperature at which the reaction occurs is increased during the course of the reaction. In this preferred modification of the process of the invention, the temperature at the beginning of the reaction, in particular up to a conversion of 80%, preferably up to a conversion of 70%, based on the weight of the alcohol used, can preferably be in the range from 90° C. to 110° C. and that towards the end of the reaction, in particular after a conversion of 80%, preferably after a conversion of 90%, based on the weight of the alcohol used, can be in the range from 115° C. to 130° C.

The process of the invention can be carried out in bulk, i.e. without use of a further solvent. If desired, an inert solvent can also be used. Such solvents include, inter alia, benzene, toluene, n-hexane, cyclohexane and methyl isobutyl ketone (MIBK) and methyl ethyl ketone (MEK).

In a particularly advantageous variant of the transesterification of the invention, all components, for example the alcohol, the methacrylic ester and the catalyst, are mixed, after which this reaction mixture is heated to boiling. The alcohol liberated, for example methanol or ethanol, can subsequently be removed from the reaction mixture by distillation, if appropriate as an azeotrope with methyl methacrylate or ethyl methacrylate.

The reaction times depend, inter alia, on the parameters selected, for example pressure and temperature. However, they are generally in the range from 1 to 24 hours, preferably from 5 to 20 hours and very particularly preferably from 6 to 12 hours. In the case of continuous processes, the residence times are generally in the range from 0.5 to 24 hours, preferably from 1 to 12 hours and very particularly preferably from 2 to 3 hours. A person skilled in the art can find further information on the reaction times in the examples attached.

The reaction can preferably take place with stirring, with the stirring rate particularly preferably being in the range from 50 to 2000 rpm, very particularly preferably in the range from 100 to 500 rpm.

The pH can be within a wide range. The reaction can advantageously be carried out at a pH in the range from 8 to 14, preferably from 9 to 13.

To prevent undesirable polymerization of the methacrylates, polymerization inhibitors can be used in the reaction. These compounds, for example hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidin-1-oxyl, p-phenylenediamine, methylene blue or sterically hindered phenols, are widely known in the art. These compounds can be used individually or in the form of mixtures and are generally commercially available. The mode of action of the stabilizers is usually that they act as free-radical scavengers for the free radicals occurring in the polymerization. Further details may be found in the relevant specialist literature, in particular Römpp-Lexikon Chemie; editors: J. Falbe, M. Regitz; Stuttgart, New York; 10th Edition (1996); key word "Antioxidantien", and the references cited here.

Preference is given to using, in particular, phenols as polymerization inhibitor. Particularly surprising advantages can be achieved when using hydroquinone monomethyl ether. Based on the weight of the total reaction mixture, the proportion of inhibitors, either individually or as a mixture, can generally be 0.01-0.5% (wt/wt).

These polymerization inhibitors can be added to the reaction mixture before or at the beginning of the reaction. Furthermore, parts of the polymerization inhibitors employed can be introduced during the transesterification. Processes in which part of the polymerization inhibitor is added via the column runback are of particular interest here. It is particularly advantageous to use, inter alia, mixtures containing methyl methacrylate, hydroquinone monomethyl ether and 4-hydroxy-2,2,6,6-tetramethylpiperidin-1-oxyl. This measure makes it possible, in particular, to avoid undesirable polymerization within the distillation column.

Furthermore, oxygen can be used for the inhibition. This can be used, for example, in the form of air, with the amounts introduced advantageously being such that the content in the gas phase above the reaction mixture remains below the explosive limit. Amounts of air in the range from 0.05 to 0.5 l per hour and mole of alcohol are particularly preferred here. In batch processes, this amount can be based on the amount of alcohol originally used. In the case of continuous processes, this amount can be based on the amount of alcohol fed in. It is likewise possible to use inert gas/oxygen mixtures, e.g. nitrogen/oxygen or argon/oxygen mixtures.

In a particular embodiment of the present invention, a combination of oxygen with at least one phenol, preferably hydroquinone monomethyl ether, can be used for inhibition.

The alcohol liberated from the (meth)acrylate used, for example methanol and/or ethanol, is separated off by distillation. Here, a mixture containing, for example, methyl methacrylate and methanol can advantageously be separated off. Surprisingly, part of the mixture which has been separated off can advantageously be recirculated to the next batch. In this modification, the proportion which can be recirculated of the mixture which has been separated off can be obtained at the end of the reaction, in particular after a conversion of 80%, preferably after a conversion of 90%, of the alcohol used. For example, the proportion of the recirculated mixture at the beginning of the next batch can be in the range from 10 to 50%, based on the total weight of methacrylic ester to be transesterified.

The transesterification can be carried out either continuously or batchwise. The addition of a low-boiling ester of (meth)acrylic acid to effect an increase in the molar ratio of low-boiling ester of (meth)acrylic acid to starting alcohol according to the invention during a continuous reaction can, for example and in particular, be carried out in plants having a plurality of reactors.

In particular, semibatch processes in which part of the reaction mixture is initially placed in the reactor are of particular interest. After commencement of the reaction, low-boiling ester of (meth)acrylic acid can be added in further steps or continuously to the reaction mixture.

In a particular embodiment, the amount of low-boiling ester of (meth)acrylic acid added can be controlled via the amount of alcohol liberated which is separated off from the reaction mixture. Control can be effected, for example, by means of the temperature which is established at an appropriate height in the column. The reflux ratio can also be set via the temperature in the column during the removal by distillation of the alcohol liberated from the starting material. If, for example, a mixture comprising methanol and methyl methacrylate is separated off from the reaction mixture, a temperature of from about 75° C. to 85° C. above which no distillate is taken off can be prescribed over a longer period of time. Only below this temperature is an appropriate amount of a mixture separated off. In this way, it is possible for a relatively high ratio of low-boiling (meth)acrylate to starting alcohol to be maintained over a long period of time without excessively large amounts of low-boiling (meth)acrylate having to be introduced into the reaction mixture.

It is important for the successful outcome according to the invention that the molar ratio of low-boiling ester of (meth)acrylic acid to starting alcohol in the reaction mixture is increased during the reaction by addition of low-boiling ester of (meth)acrylic acid. The expression "addition of low-boiling ester" means that this compound is introduced from an external source. A pure reflux which occurs within the distillation column accordingly does not constitute an addition. In particular, processes in which the molar ratio of the amount of low-boiling ester of (meth)acrylic acid to the amount of the alcohol used for the transesterification in the reaction mixture is increased by at least 10%, particularly preferably by at least 40% and very particularly preferably by at least 100%, during the reaction by addition of low-boiling ester of (meth)acrylic acid are of particular interest. For example, the molar ratio of the low-boiling ester added during the reaction to the amount of the low-boiling ester used at the beginning of the reaction can be in the range from 1:5 to 2:1, particularly preferably from 1:3 to 1:1.5. The weight ratio of starting alcohol to the low-boiling ester of (meth)acrylic acid at the beginning of the reaction can preferably be in the range from 1:2 to 1:8, particularly preferably from 1:2.5 to 1:6 and very particularly preferably in the range from 1:3 to 1:4. As a result of addition of low-boiling ester during the reaction, this ratio can be increased, for example, to from 1:3 to 1:20, preferably from 1:4 to 1:15 and very particularly preferably from 1:6 to 1:10. These values are in each case based on the starting alcohol present in the reaction mixture. The proportion of the starting alcohol which has been converted into the product ester can frequently be determined from the proportion of alcohol which has been liberated as a result of the reaction and been distilled off. Furthermore, the proportion of starting alcohol present in the reaction mixture can be determined by gas chromatography.

The addition of the low-boiling ester of (meth)acrylic acid can advantageously be carried out over a period of time which corresponds to at least 30%, preferably at least 50% and very particularly preferably at least 70%, of the reaction time. Here, the addition can be carried out in steps within this period of time, with the first addition setting the beginning of this period of time and the last addition setting the end of this period of time. The addition is preferably carried out in at least three, preferably at least 5 and very particularly preferably at least 10, steps. Furthermore, this addition can also be carried out continuously.

Batch processes in which methyl methacrylate is added during the transesterification are, inter alia, of particular interest. This embodiment is advantageous, for example, if methyl methacrylate is removed together with methanol from the reaction mixture. The weight ratio of the amount of methyl methacrylate added during the transesterification to the amount of methanol/methyl methacrylate mixture separated off can preferably be in the range from 2:1 to 1:2, particularly preferably from 1.5:1 to 1:1.5.

In the case of batch processes, excess starting material, in particular the unreacted ester of (meth)acrylic acid, can be separated off by distillation towards the end of the reaction. This too can be reused without further purification in the next batch.

The distillate obtained at the beginning of the reaction, which can, for example, comprise large amounts of methanol or ethanol, can likewise be recycled, for example by introduction into a coupled plant for preparing the (meth)acrylate ester to be transesterified.

A suitable plant for carrying out the present transesterification can comprise, for example, a stirred tank reactor provided with agitator, steam heating, distillation column and condenser. Such plants are known per se and are described, for example, in Ullmann's Encyclopedia of Industrial Chemistry (6th Edition), Verlag Wiley-VCH, Weinheim 2003, Volume 10, page 647. The size of the plant depends on the amount of (meth)acrylate to be prepared, with the present process being able to be carried out either on a laboratory scale or on an industrial scale. According to a particular aspect, the stirred tank reactor can accordingly have a tank volume in the range from 1 $m^3$ to 30 $m^3$, preferably from 3 $m^3$ to 20 $m^3$. The agitator of the reactor tank can, in particular, be configured in the form of an anchor stirrer, impeller, paddle stirrer or Inter-MIG stirrer.

The task of the distillation column is to ensure that a methanol- or ethanol-rich azeotrope is taken off in order to minimize the losses of starting ester which is inevitably discharged. The distillation column can have one, two or more separation stages. The number of separation stages is the number of trays in the case of a tray column or the number of theoretical plates in the case of a column containing ordered packing or random packing elements. Examples of trays in a multistage distillation column are bubblecap trays, sieve trays, tunnel trays, valve trays, slotted trays, sieve-slotted trays, sieve-bubblecap trays, nozzle trays, centrifugal trays, examples of random packing elements in a multistage distillation column are Raschig rings, Lessing rings, Pall rings, Berl saddles, Intalox saddles, and examples of ordered packing in a multistage distillation column are Mellapak (Sulzer), Rombopak (Kühni), Montz-Pak (Montz). Conversion-dependent adaptation of the reflux ratio enables, for example when using methyl methacrylate, a proportion of methanol in the distillate which is above 60% to be obtained over a wide conversion range.

Suitable condensers which can be present in the plant for carrying out the present transesterification include, inter alia, plate heat exchangers and shell-and-tube heat exchangers.

After the reaction is complete, the (meth)acrylate obtained frequently meets the exacting requirements indicated above, so that further purification is frequently not necessary. To increase the quality further and, in particular, to separate off the catalyst, the mixture obtained can be purified by known methods.

In an embodiment of the process of the invention, the product mixture obtained can be purified by means of filtration processes. These processes are known from the prior art (W. Gösele, Chr. Alt in Ullmann's Encyclopedia of Industrial Chemistry (6th Edition), Verlag Wiley-VCH, Weinheim 2003, Volume 13, pages 731 and 746), which can be carried out using customary filtration aids such as bleaching earth and/or aluminium silicate (Perlite). For example, it is possible to use, inter alia, continuously operable filters for a washcoat filtration or candle filters.

A further improvement in the quality of the product can be achieved, for example, by distillation of the filtrate obtained. Owing to the tendency of the monomer to polymerize, distillation processes in which the thermal stress on the substance to be distilled is minimized are advisable. Apparatuses in which the monomer is continuously vaporized from a thin layer, e.g. falling film evaporators and evaporators having a rotating wiper system, are well suited. Short path evaporators can also be used. Such apparatuses are known (Ullmann's Encyclopedia of Industrial Chemistry (6th Edition), Verlag Wiley-VCH, Weinheim 2003, Volume 36, page 505). Thus, for example, a continuous evaporator having a rotating wiper system and a superposed column can be used. The distillation can, for example, be carried out at a pressure in the range from 1 to 40 mbar and an evaporator temperature of from 120° C. to 150° C.

The present invention is illustrated below with the aid of examples and comparative examples, without this constituting a restriction.

COMPARATIVE EXAMPLE 1

600 kg of trimethylolpropane, 3348 kg of methyl methacrylate (MMA), 0.1 kg of hydroquinone monomethyl ether as inhibitor and a mixture of 5 kg of calcium oxide and 1 kg of lithium chloride as catalyst are combined in a 6 m$^3$ stirred tank reactor provided with agitator, steam heating, distillation column and condenser and the mixture is stirred while passing in air. To stabilize the column, a total of 151 kg of MMA containing 0.12 kg of hydroquinone monomethyl ether and 0.016 kg of 4-hydroxy-2,2,6,6-tetramethylpiperidin-1-oxyl in dissolved form are introduced into the column runback during the course of the reaction. The apparatus is heated to a temperature at the bottom of 96° C., with the column initially being operated under total reflux. As soon as the temperature at the top of the column drops below 70° C., the methanol/MMA mixture is taken off at a reflux ratio of 8:1. Above a temperature at the top of the column of 85° C., the methanol/MMA mixture is low in methanol and is collected in a separate vessel for reuse as raw material in the next batch. When a temperature at the bottom of 115° C. has been reached, the reaction is complete and excess MMA is taken off under reduced pressure, with the pressure gradually being reduced to 100 mbar. When no more MMA distills off, the vacuum is broken. The contents of the tank, which comprise the catalyst-containing trimethylpropane trimethacrylate, are admixed with 15 kg of bleaching earth and 5 kg of aluminium silicate (Perlite) as filter aid and freed of the catalyst by washcoat filtration. The filtrate is fed into a continuous evaporator (area: 2 m$^2$) having a rotating wiper system at a pressure of 15 torr and an evaporator temperature of 142° C. A total of 1420 kg of trimethylolpropane trimethacrylate are obtained from the bottom product.

| Composition (determined by gas chromatography): | |
|---|---|
| 90.6% | of trimethylolpropane trimethacrylate |
| 0.031% | of MMA |
| 0.09% | of trimethylolpropane monomethacrylate |
| 2% | of trimethylolpropane dimethacrylate |
| 2.4% | of 2-{[2-(methoxycarbonyl)propoxy]methyl}-2-[(2-methylprop-2-enoyloxy)methyl]butyl 2-methylprop-2-enoate |
| 3.5% | of 2-{[2-({2,2-bis[(2-methylprop-2-enoyloxy)methyl]butyl}oxy-carbonyl)propoxy]methyl}-2-[(2-methylprop-2-enoyloxy)methyl]butyl 2-methylprop-2-enoate |

Example 1

775 kg of trimethylolpropane, 1018 kg of methyl methacrylate (MMA) and also 1433 kg of recycled MMA from Comparative Example 1, 0.123 kg of hydroquinone monomethyl ether as inhibitor and a mixture of 10 kg of calcium oxide and 2.5 kg of lithium chloride as catalyst are combined in a 6 m$^3$ stirred tank reactor provided with agitator, steam heating, distillation column and condenser and the mixture is stirred while passing in air. To stabilize the column, a total of 151 kg of MMA containing 0.12 kg of hydroquinone monomethyl ether and 0.016 kg of 4-hydroxy-2,2,6,6-tetramethylpiperidin-1-oxyl in dissolved form are introduced into the column runback during the course of the reaction. The apparatus is heated to a temperature at the bottom of 100° C., with the column initially being operated under total reflux. As soon as the temperature at the top of the column drops below 70° C., the methanol/MMA mixture is taken off at a reflux ratio of 4:1. The MMA stock in the reactor is supplemented by introduction of equal parts of fresh MMA per part of methanol/MMA mixture taken off. A total of 1414 kg of MMA are in this way introduced over a period of 5 hours. Over a period of 8 hours, the reflux ratio is adapted to the decreasing formation of methanol to 27:1. A total of 1410 kg of methanol/MMA mixture are discharged. Above a temperature at the top of the column of 85° C., the methanol/MMA mixture is low in methanol and is collected in a separate vessel for reuse as raw material in the next batch. At a temperature at the bottom of 115° C., the reaction is complete and excess MMA is taken off under reduced pressure, with the pressure gradually being reduced to 100 mbar. When no more MMA distills off, the vacuum is broken. The contents of the tank, which comprise the catalyst-containing trimethylpropane trimethacrylate, are admixed with 18 kg of bleaching earth and 12 kg of aluminium silicate (Perlite) as filter aid and freed of the catalyst by washcoat filtration. The filtrate is fed into a continuous evaporator (area: 3.5 m$^2$) having a rotating wiper system at a pressure of 18 torr and an evaporator temperature of 134° C. A total of 1830 kg of trimethylolpropane trimethacrylate are obtained from the bottom product.

| Composition (determined by gas chromatography): | |
|---|---|
| 93.6% | of trimethylolpropane trimethacrylate |
| 0.1% | of MMA |
| 0.09% | of trimethylolpropane monomethacrylate |
| 0.66% | of trimethylolpropane dimethacrylate |
| 1.8% | of 2-{[2-(methoxycarbonyl)propoxy]methyl}-2-[(2-methylprop-2-enoyloxy)methyl]butyl 2-methylprop-2-enoate |
| 2.9% | of 2-{[2-({2,2-bis[(2-methylprop-2-enoyloxy)methyl]butyl}oxy-carbonyl)propoxy]methyl}-2-[(2-methylprop-2-enoyloxy)methyl]butyl 2-methylprop-2-enoate |

The invention claimed is:

1. A process for preparing a (meth)acrylate, comprising:
    transesterifying an alcohol with a low-boiling ester of (meth)acrylic acid in the presence of a transesterification catalyst, and
    separating by distillation the alcohol liberated from the low-boiling ester of (meth)acrylic acid,
    wherein the molar ratio of low-boiling ester of (meth)acrylic acid to starting alcohol present in the reaction mixture is increased during the reaction by addition of low-boiling ester of (meth)acrylic acid;
    wherein the molar ratio of the low-boiling ester added during the reaction to the amount of the low-boiling ester present at the beginning of the reaction is in the range from 1:5 to 2:1.

2. The process according to claim 1, wherein the low-boiling ester of (meth)acrylic acid is methyl(meth)acrylate or ethyl (meth)acrylate or both.

3. The process according to claim 1, wherein the low-boiling ester of (meth)acrylic acid is methyl methacrylate.

4. The process according to claim 1, wherein the starting alcohol is a polyhydric alcohol.

5. The process according to claim 4, wherein the alcohol is ethylene glycol, trimethylolpropane, 1,2-propanediol, 1,3-propanediol, 1,3-butanediol, 1,4-butanediol, 1,6-hexanediol or pentaerythritol, or mixtures thereof.

6. The process according to claim 1, wherein the catalyst is at least one lithium compound or at least one calcium compound, or a mixture thereof, wherein at least one of the compounds of lithium or of calcium is an oxide, a hydroxide, an alkoxide having from 1 to 4 carbon atoms or a carboxylate having from 1 to 4 carbon atoms.

7. The process according to claim 1, wherein the catalyst comprises a mixture comprising lithium chloride and calcium oxide.

8. The process according to claim 1, wherein the addition is carried out over a period of time which corresponds to at least 50% of the reaction time.

9. The process according to claim 1, wherein the amount of low-boiling ester of (meth)acrylic acid added is controlled via the amount of alcohol liberated which is separated off from the reaction mixture.

10. The process according to claim 9, wherein the amount of alcohol liberated which is separated off from the reaction mixture is controlled of the temperature in the column of the distillation.

11. The process according to claim 1, wherein the molar ratio of low-boiling ester of (meth)acrylic acid to starting alcohol present in the reaction mixture is increased by at least 40% during the reaction by addition of low-boiling ester of (meth)acrylic acid.

12. The process according to claim 1, wherein a mixture comprising methyl methacrylate and methanol is separated off.

13. The process according to claim 1, wherein methyl methacrylate is added during said transesterifying.

14. The process according to claim 13, wherein the weight ratio of the amount of methyl methacrylate added during said transesterifying to the amount of methanol/methyl methacrylate mixture separated off is in the range from 2:1 to 1:2.

15. The process according to claim 1, wherein the reaction time is in the range from 5 to 20 hours.

16. The process according to claim 15, wherein the reaction time is in the range from 6 to 12 hours.

17. The process according to claim 1, wherein the weight ratio of starting alcohol to low-boiling ester of (meth)acrylic acid is in the range from 1:2 to 1:20.

18. The process according to claim 17, wherein the weight ratio of starting alcohol to low-boiling ester of (meth)acrylic acid is in the range from 1:5 to 1:15.

19. The process according to claim 1, wherein the reaction is carried out at a pressure in the range from 200 to 2000 mbar.

20. The process according to claim 1, wherein the reaction is carried out at a temperature in the range from 90° C. to 130° C.

21. The process according to claim 1, wherein the temperature at which the reaction occurs is increased during the course of the reaction.

22. The process according to claim 20, wherein the temperature at the beginning of the reaction is in the range from 90° C. to 110° C. and the temperature towards the end of the reaction is in the range from 115° C. to 130° C.

23. The process according to claim 1, wherein the reaction is carried out in the presence of a polymerization inhibitor.

24. The process according to claim 1, wherein the reaction further comprises introducing oxygen.

25. The process according to claim 21, wherein the temperature at the beginning of the reaction is in the range from 90° C. to 110° C. and the temperature towards the end of the reaction is in the range from 115° C. to 130° C.

26. The process according to claim 1, wherein the catalyst is a transesterification catalyst.

27. The process according to claim 1, wherein the catalyst comprises
  (i) at least one lithium compound selected from the group consisting of lithium chloride (LiCl), lithium amide (LiNH$_2$), lithium oxide (Li$_2$O), lithium hydroxide (LiOH), lithium methoxide (Li(CH$_3$O)), lithium ethoxide (Li(CH$_3$CH$_2$O)), and lithium acetate, and
  (ii) at least one calcium compound selected from the group consisting of calcium oxide (CaO), calcium hydroxide (Ca(OH)$_2$), calcium methoxide (Ca(CH$_3$O)$_2$), calcium ethoxide (Ca(CH$_3$CH$_2$O)$_2$), and calcium acetate.

28. The process according to claim 1, wherein the catalyst comprises
  a mixture comprising
  a) lithium hydroxide and calcium oxide, or
  b) lithium hydroxide and calcium hydroxide.

29. The process according to claim 1, wherein the catalyst comprises
  a mixture comprising lithium amide (LiNH$_2$) and lithium chloride (LiCl).

30. A process for preparing a (meth)acrylate, comprising:
  transesterifying an alcohol with a low-boiling ester of (meth)acrylic acid in the presence of a transesterification catalyst, and
  separating by distillation the alcohol liberated from the low-boiling ester of (meth)acrylic acid,
  wherein the molar ratio of low-boiling ester of (meth)acrylic acid to starting alcohol present in the reaction mixture is increased during the reaction by addition of low-boiling ester of (meth)acrylic acid,
  wherein a weight ratio of starting alcohol to the low-boiling ester of (meth)acrylic acid at the beginning of the reaction is from 1:2 to 1:8 and wherein said weight ratio increases as a result of addition of low-boiling ester during the reaction to from 1:3 to 1:20.

31. A process according to claim 30, wherein the catalyst comprises:
  (i) lithium amide (LiNH$_2$) or lithium acetate in combination with
  at least one lithium compound selected from the group consisting of lithium chloride (LiCl), lithium amide (LiNH$_2$), lithium oxide (Li$_2$O), lithium hydroxide (LiOH), lithium methoxide (Li(CH$_3$O)), lithium ethoxide (Li(CH$_3$CH$_2$O)), and lithium acetate, and
  (ii) at least one calcium compound selected from the group consisting of calcium oxide (CaO), calcium hydroxide (Ca(OH)$_2$), calcium methoxide (Ca(CH$_3$O)$_2$), calcium ethoxide (Ca(CH$_3$CH$_2$O)$_2$), and calcium acetate.

* * * * *